United States Patent
Stasney et al.

(10) Patent No.: US 7,024,711 B1
(45) Date of Patent: Apr. 11, 2006

(54) SONOGRAPHY BED HAVING PATIENT SUPPORT AND SONOGRAPHER ACCESS PROVISIONS

(76) Inventors: T. Glen Stasney, 10752 Co. Rd. 8070, West Plains, MO (US) 65775; Jason K. Stasney, 2508 Co. Rd. 6560, Pottersville, MO (US) 65790

( * ) Notice: Subject to any disclaimer, the term of this patent is extended or adjusted under 35 U.S.C. 154(b) by 0 days.

(21) Appl. No.: 10/449,429

(22) Filed: May 30, 2003

Related U.S. Application Data

(63) Continuation-in-part of application No. 10/325,684, filed on Dec. 19, 2002, now abandoned, which is a continuation-in-part of application No. 09/943,545, filed on Aug. 30, 2001, now abandoned.

(60) Provisional application No. 60/229,823, filed on Aug. 31, 2000, provisional application No. 60/342,547, filed on Dec. 20, 2001.

(51) Int. Cl.
*A61G 13/08* (2006.01)
*A61B 6/04* (2006.01)
*A47B 7/00* (2006.01)

(52) U.S. Cl. .................. 5/613; 5/601; 5/617; 5/610; 5/634; 5/635; 378/209

(58) Field of Classification Search .............. 5/601, 5/613, 617, 616, 614, 610, 634, 635, 607, 5/608; 378/209
See application file for complete search history.

(56) References Cited

U.S. PATENT DOCUMENTS

| | | | | |
|---|---|---|---|---|
| 1,626,091 A | * | 4/1927 | Macklin | 5/618 |
| 2,845,543 A | * | 7/1958 | Hansen et. al. | 378/209 |
| 3,868,103 A | * | 2/1975 | Pageot et al. | 5/614 |
| 4,195,829 A | * | 4/1980 | Reser | 5/614 |
| 4,387,888 A | * | 6/1983 | Marinakis | 5/617 |
| 4,865,303 A | * | 9/1989 | Hall | 5/614 |
| 4,872,657 A | * | 10/1989 | Lussi | 5/608 |
| 4,973,034 A | | 11/1990 | Michele | 269/324 |
| 5,040,546 A | | 8/1991 | Deluhery | 128/845 |
| 5,184,363 A | | 2/1993 | Falbo, Sr. | 5/601 |
| 5,208,928 A | * | 5/1993 | Kuck et al. | 5/608 |

(Continued)

OTHER PUBLICATIONS

The Bundle Block. from www.redbudmedical.com/the_bundle_block.htm. undated but available for sale since 1992 per manufacturer. 1 page.

(Continued)

*Primary Examiner*—Katherine Mitchell
(74) *Attorney, Agent, or Firm*—Jonathan A. Bay

(57) ABSTRACT

A patient exam bed useful for sonograms including echocardiography exams has a mattress provided with one or more pop-up wedges as well as one or more access bays formed through a side edge of the mattress. The access bays provide reach up access to a patient from below a plane of the mattress top, and can be filled-in when not needed by movable or removable in-fill sections. The pop-up wedges act to chock or support a patient to hold steady in a specific angle-of-roll or attitude chosen from various angles of lying down on one's side. The mattress optionally might have one or more folding sections to convert the bed into more like a chair or reclining chair. Additionally, any of the various foregoing options may be enhanced with power equipment to drive the movable components through their movements.

19 Claims, 11 Drawing Sheets

U.S. PATENT DOCUMENTS

| | | | |
|---|---|---|---|
| 5,461,739 A | 10/1995 | Falbo, Sr. | 5/607 |
| 5,678,263 A | 10/1997 | Berthe | 5/600 |
| 5,754,997 A * | 5/1998 | Lussi et al. | 5/618 |
| 5,919,131 A * | 7/1999 | Smoler et al. | 600/300 |
| 5,950,262 A * | 9/1999 | Smoler et al. | 5/613 |
| 6,062,648 A * | 5/2000 | Adler | 297/440.24 |
| 6,202,230 B1 * | 3/2001 | Borders | 5/618 |
| 6,353,949 B1 * | 3/2002 | Falbo | 5/610 |
| 6,367,104 B1 * | 4/2002 | Falbo et al. | 5/601 |

OTHER PUBLICATIONS

Factors to consider when choosing a supine bike echocardiography bed. from www.redbudmedical.com/choosing_a_bed.htm. undated but available prior to 2000 per manufacturer. 5 pages.

Stress Echo Update. Vol. 8 No. 3. "Advantages of of Utilizing a Specialized Table for Routine Echiocardography." Jun. 1988. 8 pages.

* cited by examiner

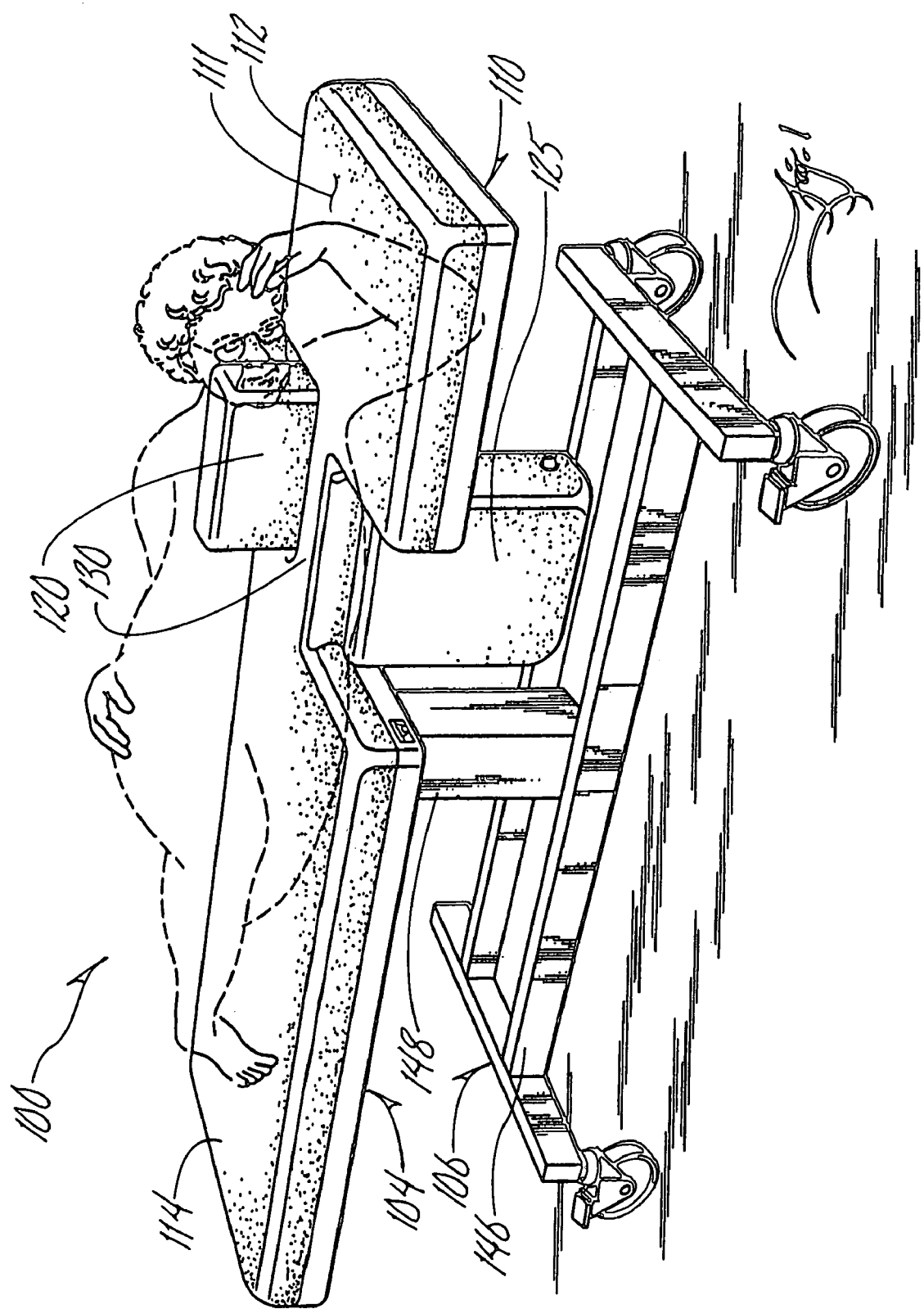

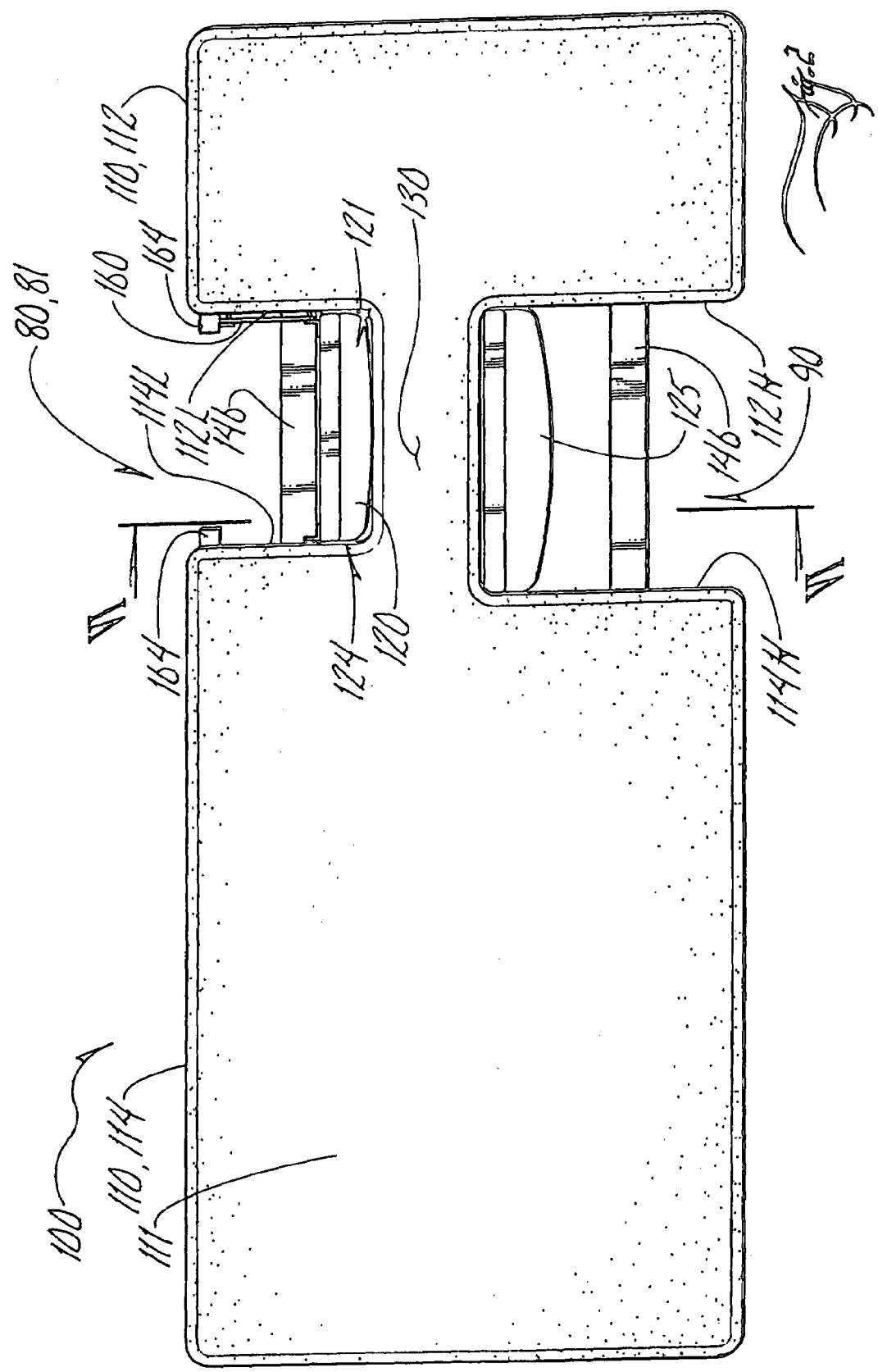

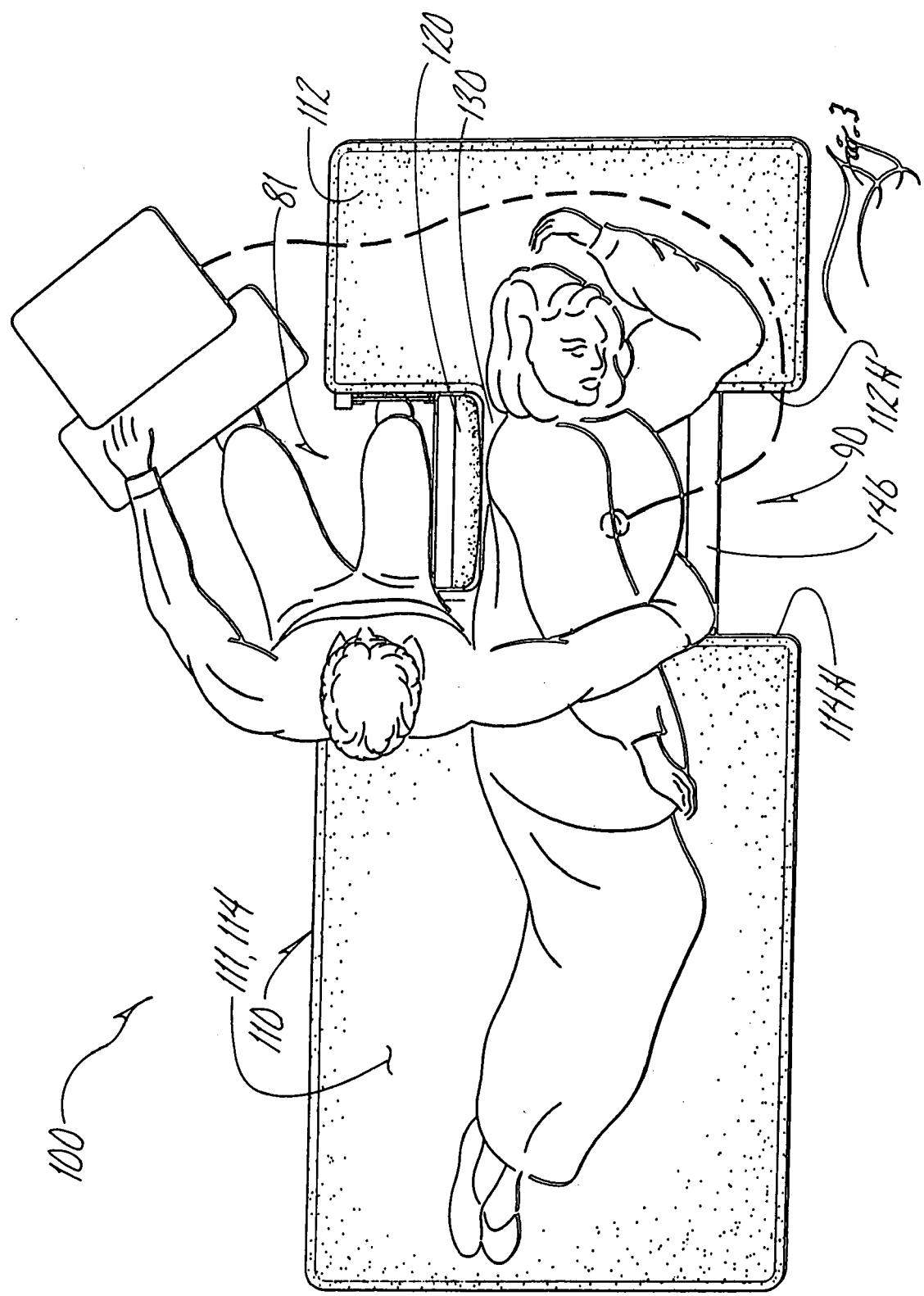

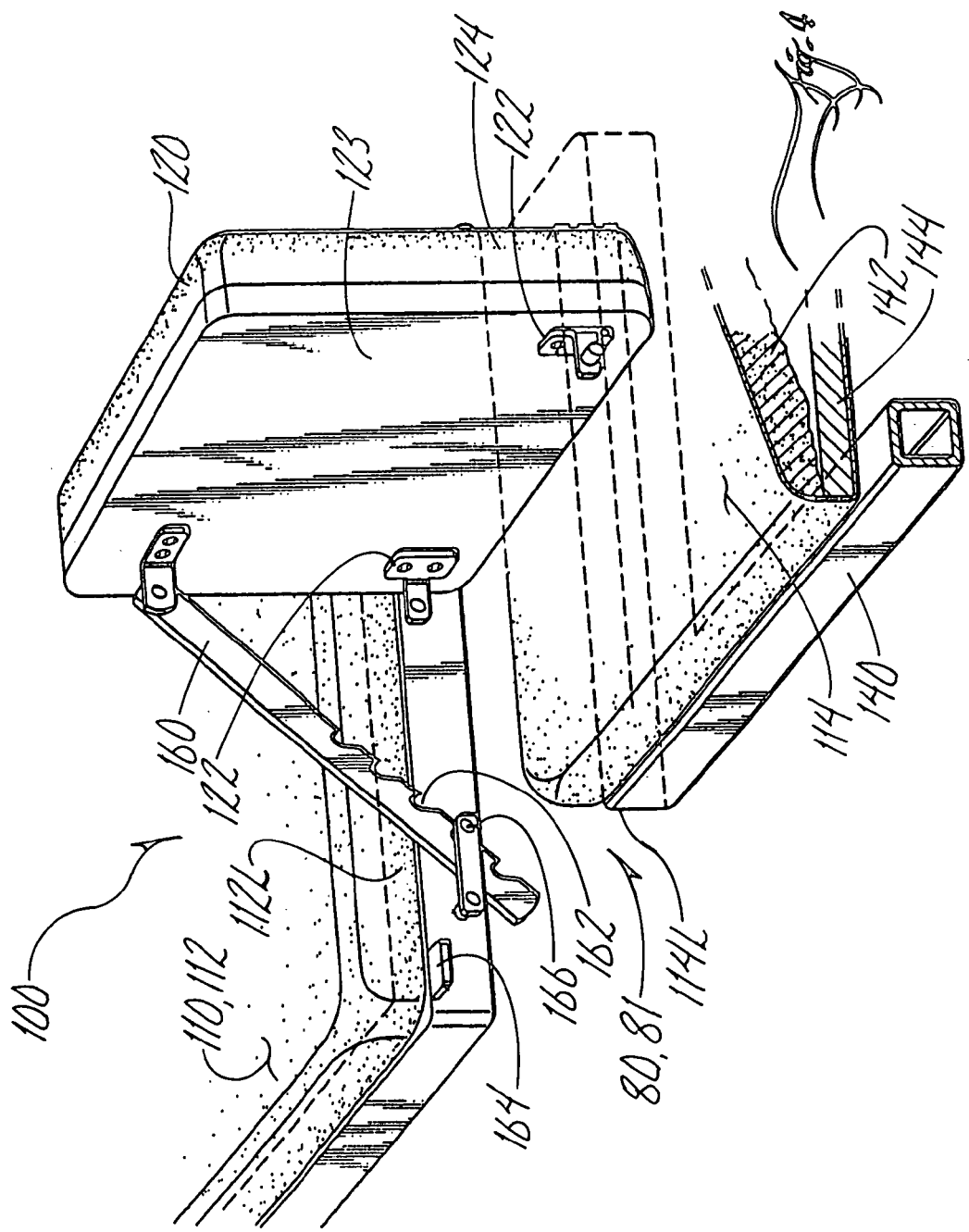

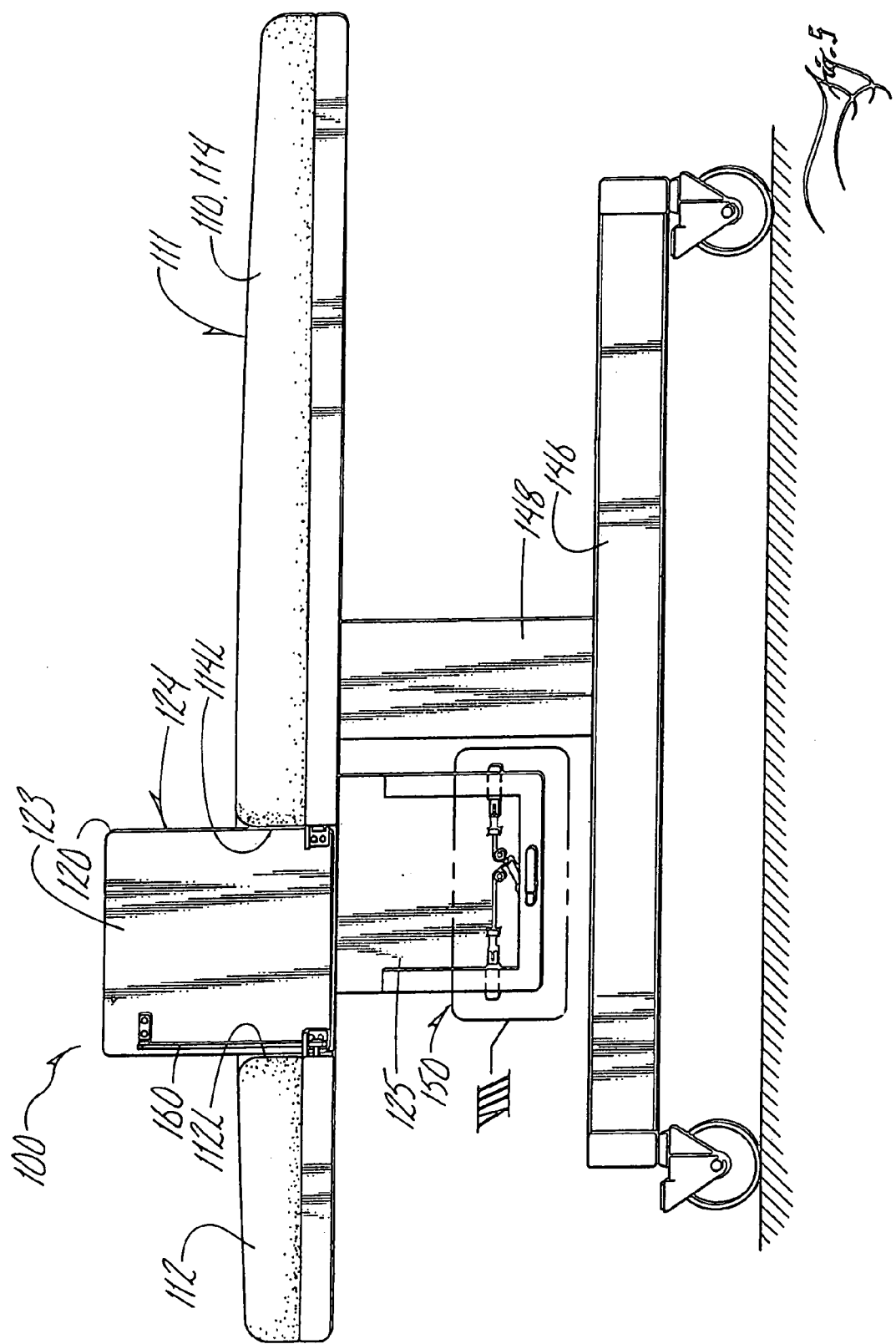

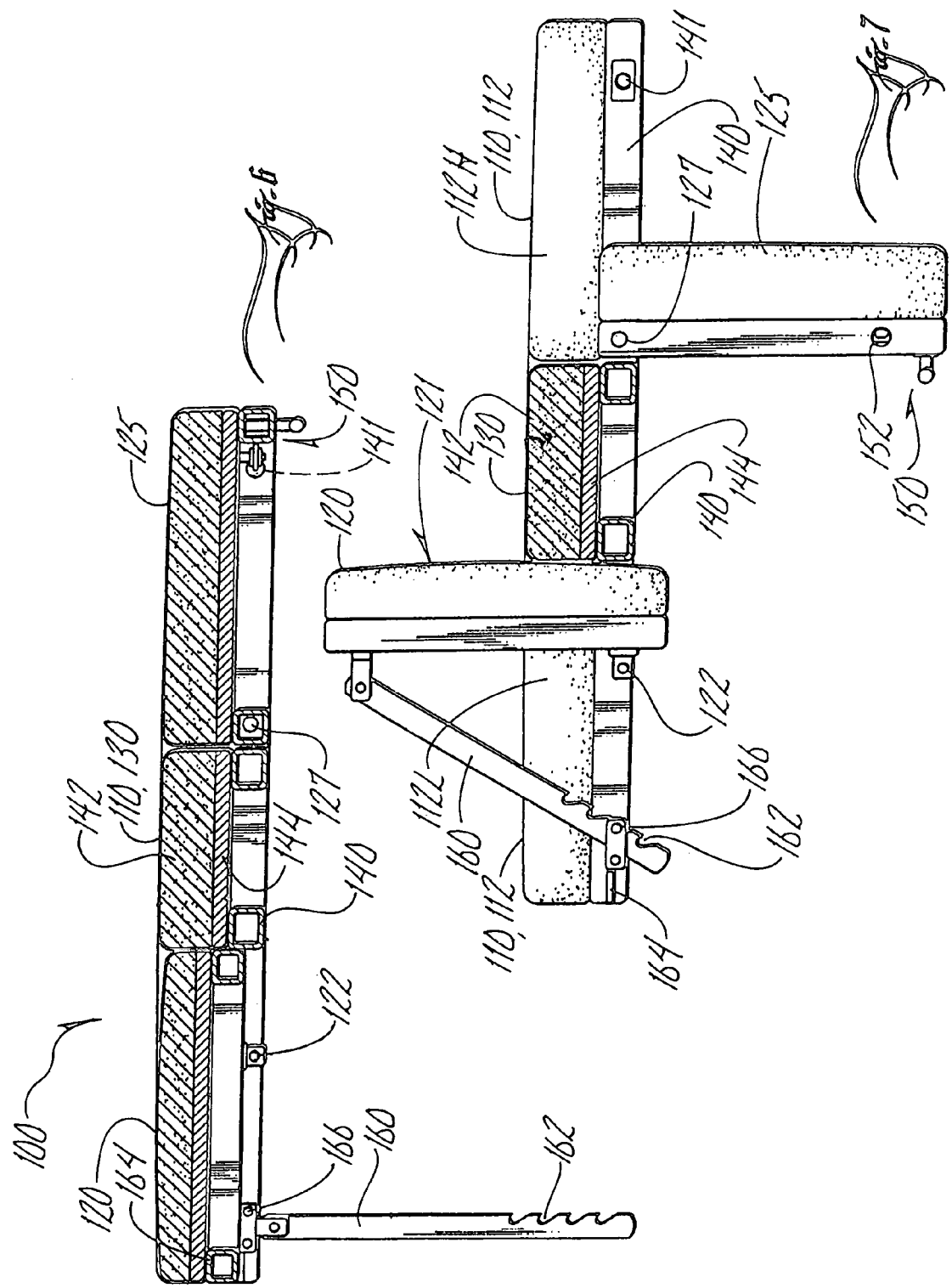

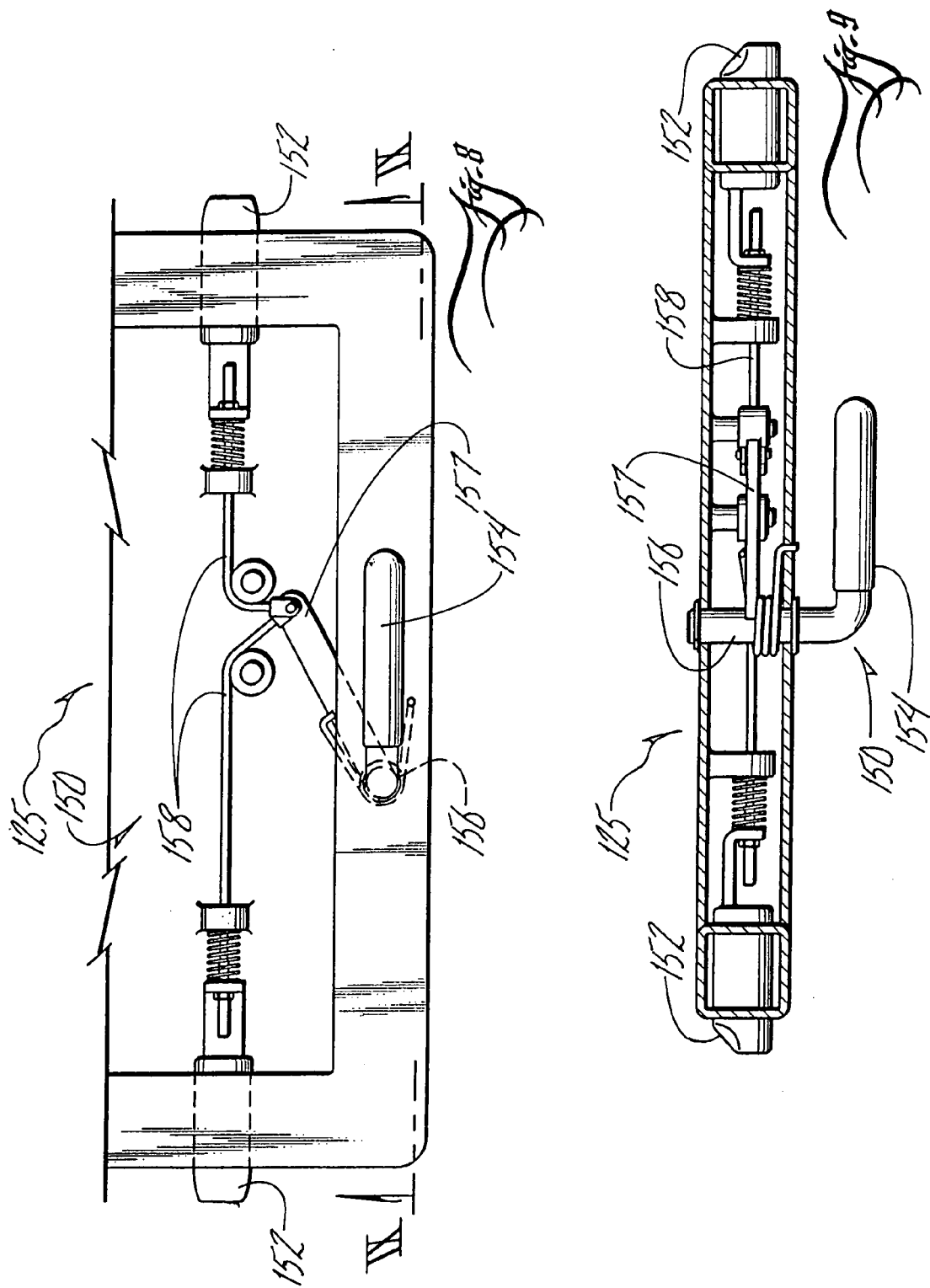

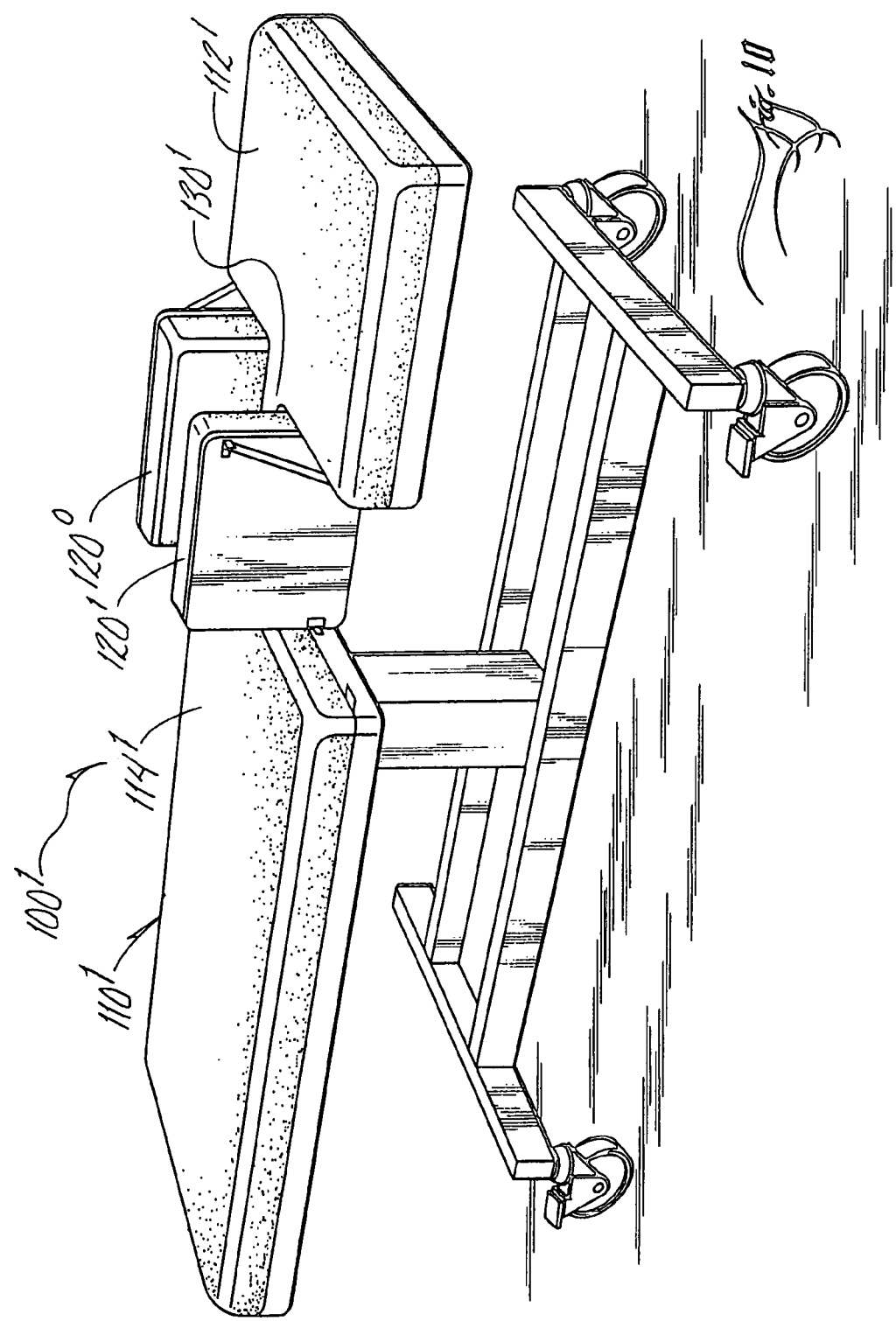

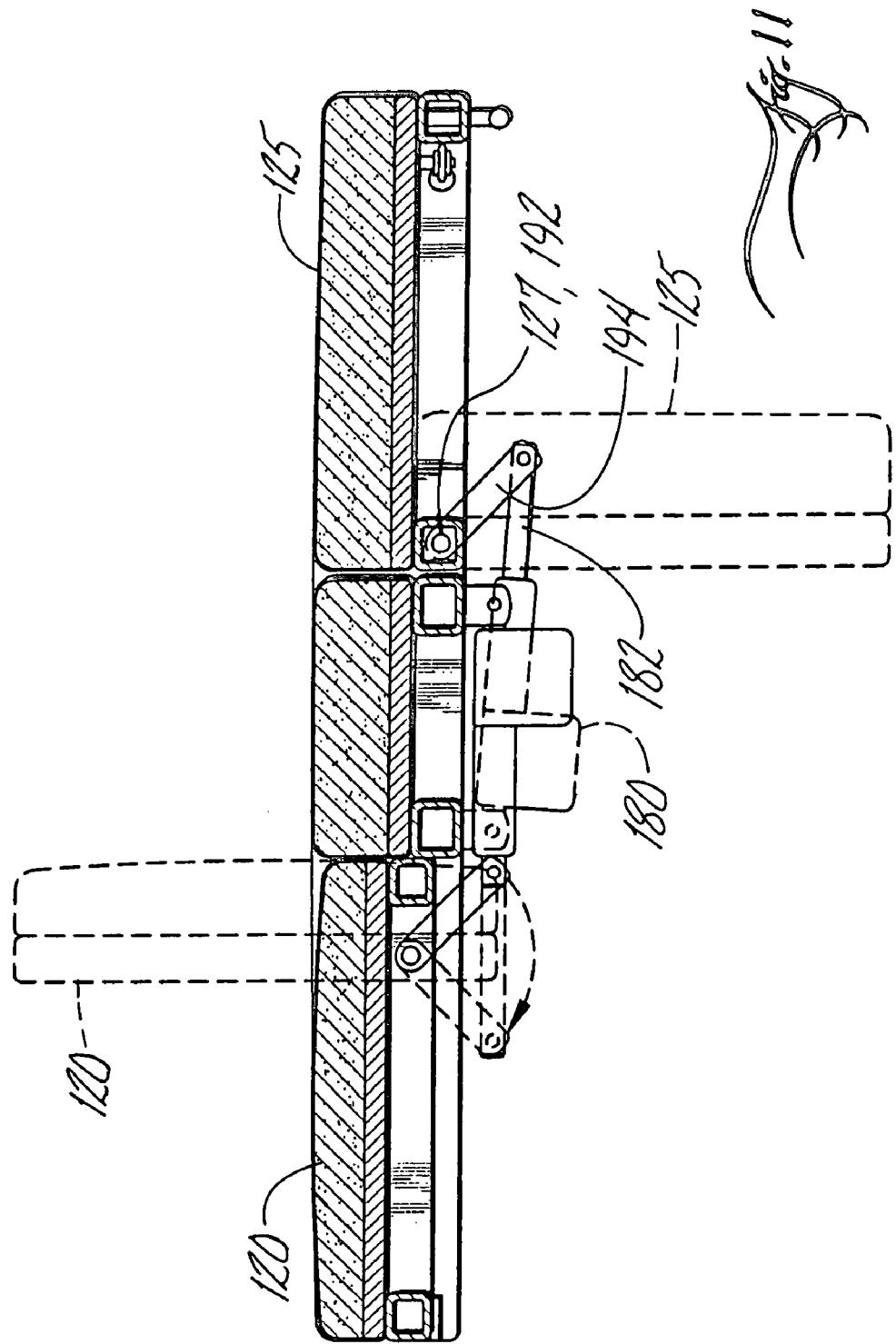

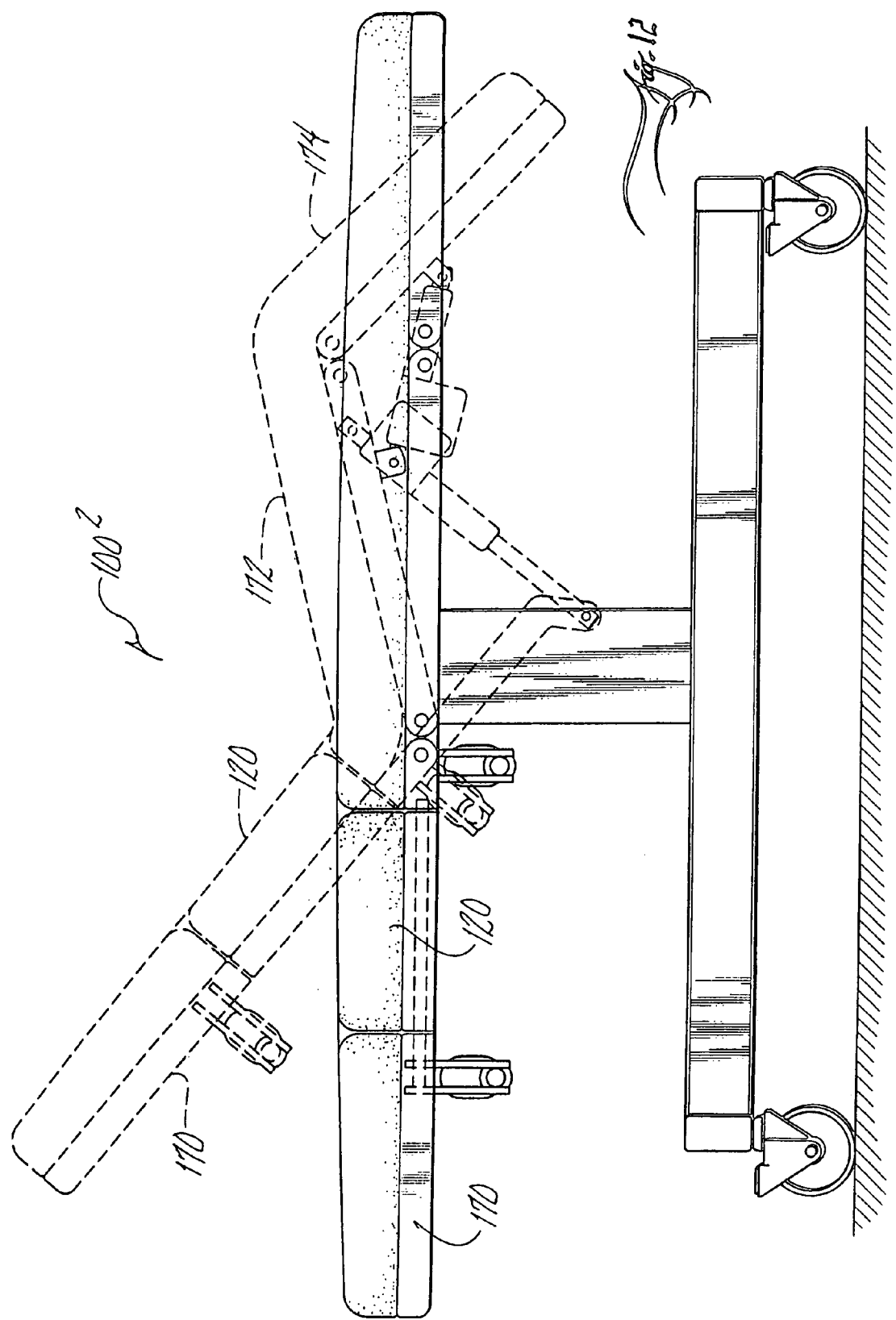

SONOGRAPHY BED HAVING PATIENT SUPPORT AND SONOGRAPHER ACCESS PROVISIONS

CROSS-REFERENCE TO RELATED APPLICATION(S)

This application is a continuation-in-part of U.S. patent application Ser. No. 10/325,684, filed Dec. 19, 2002 now abandoned, which claims the benefit of U.S. Provisional Application No. 60/342,547, filed Dec. 20, 2001, and which also is a continuation-in-part of U.S. patent application Ser. No. 09/943,545, filed Aug. 30, 2001 now abandoned, which claims the benefit of U.S. Provisional Application No. 60/229,823, filed Aug. 31, 2000. All the foregoing patent documents are incorporated by reference.

BACKGROUND OF THE INVENTION

1. Field of the Invention

The invention relates to patient beds and tables and, more particularly, to a sonography bed or table having patient support and sonographer access provisions.

In the field of cardiology, sonography exams are sometimes given a more particular name, ie., echocardiography exam. In other fields say gynecology and so on, such exams are simply referenced by the more generalized name, sonogram or sonography exam. A bed in accordance with the invention is provided with an inventive top having any of various options such as and without limitation (i) one or more pop-up wedges, (ii) one or more access bays formed through the bed's lateral edge, any of which access bays, during times of non-use, (iii) are equipped to be filled in by movable or removable flaps. The inventive bed might further include the option of having (iv) one or more folding sections to convert the bed into more like a reclining chair or chaise longue. Additionally, any of the various foregoing options may be enhanced with power equipment to drive the movable components (if any) through their movements. In use for echo-cardiography (among other uses), a pop-up wedge facilitates supporting a patient to hold steady in a specific attitude (ie., of roll) on one's side, or in technical language, in a lateral decubitus position.

A number of additional features and objects will be apparent in connection with the following discussion of preferred embodiments and examples.

2. Prior Art

The reference of U.S. Pat. No. 5,184,363—Falbo, Sr., discloses an echo-cardiography bed having dual drop sections. More particularly, the bed has a mattress top that includes two drop-out sections. A principal drop-out section is located on the bed's left-side for exposing underneath a patient lying on his or her left side. The exposed portion of the patient is the heart region of the patient's left-side rib cage. This location of the principal drop-out section allows an examiner to reach up and rub a sonographic probe against the exposed left side of the rib cage. According to the reference, the other drop-out section is located to provide an opening for the examiner to use, to accommodate the examiners legs during the examination.

The text of the reference recites:—"The [examiner] may then stand in [this other] opening, or sit on mattress with the [examiner]'s legs within the opening [to do the exam]. . . . " See, eg., the Abstract.

By way of background, echocardiography exams are one tool among others that allow diagnosis of the heart's health. Typically, a patient is asked to exercise (as on a treadmill) in order to elevate the heartbeat. Then the patient is stopped and examined immediately by an echocardiography procedure. Standardized guidelines impose a window of opportunity of only forty-five seconds or so to acquire data for a procedure known as "stress echo" or the like (although, other procedures may extend over twenty minutes). The "stress echo" exam has to be completed so swiftly because the elevated heartbeat falls away within two minutes or so (ie., after exercise is quit and not once data acquisition starts; there is a lag between exercise quit time and data acquisition start time).

The general practice in the art is to have the patient to lie down for the exam on his or her left side. Perhaps this posture causes the heart to fall against (or near) the left side of the rib cage. That way, maybe the sensitive sonograph probes that are rubbed against the left-side heart region of the rib cage can get better results.

The above-referenced patent of Falbo, Sr., discloses an exam bed having at least a principal drop-out section. Knowing the foregoing brief sketch of cardiography exams helps understanding the purpose of the principal drop-out section. The fixed part of the bed's mattress supports the stretched out patient while the principal drop-out section exposes the patient's left-side heart region of the rib cage. Exposing the patient's left-side heart region allows the examiner access to rub the sonograph probes.

To move over to another matter, the Falbo, Sr., reference also discloses a subordinate drop-out section on the opposite side of the bed. As stated, "The [examiner] may then stand in [this subordinate] opening, or sit on mattress with the [examiner]'s legs within the opening [to do the exam]. . . . " See, eg., the Abstract.

More specifically, standing or sitting on the opposite side of the bed to do the exam presents challenges that right-handed examiners have to deal with. Such challenges include that, standing or sitting on the opposite side of the bed to do the exam entails reaching over and wrapping one's arms completely around the patient in order to rub the probe. How the probe is worked can be better envisioned by any of us by thinking of holding a coffee mug in our right hand by the handle, and rubbing the top of mug under the seat of a chair in which we sit. Except that, curled in our arm is a stretched out patient. Some right-handed examiners choose to do as left-handed examiners do, and work on the same side of the bed as the patient, either by learning sufficient dexterity with the probe in the left hand, or by suffering through an awkward posture whereby the right elbow is dropped low out to the side of the hip and then twisted upwards.

Those right-handed examiners who choose to work from the opposite side of the bed confront numerous challenges for choosing so. Frequently these kinds of patients are so obese that it is uncomfortable, inter-personally as well as physically, to wrap one's arm around them.

The prior art echocardiography beds have presented a number of shortcomings. For one, many of these patients are suffering severely from the effects of stroke or cardiac disease. They are weak, unsteady, and helpless in helping themselves maneuvering as required—ie., from pacing the treadmill, to hopping onto the bed, and then stretching out and holding still in the reclining or lateral decubitus position—even if they most ardently wanted to help themselves. Given the time constraint, the examiner must use the time efficiently both to get the patient stretched out onto his or her side and then get the exam underway. One problem examiners face is finding that—after having steadied the patient in good position for examination, then—the patient can't steady him or herself alone when let go. Whereas patients are asked to lie on their left side as a general proposition, examiners are quite particular as to the exact position they want for any given patient. This depends on factors ranging from (i) the examiner's choice to (ii) the figure and proportions of the patient.

Examiners adjust each patient swift as possible—into that examiner's favorite position, as for that particular patient, and at that particular instance of an examination—in order not to waste any time. Examiners then would like to be able to let completely go in order to turn their complete attention next on manipulating the test equipment. The position the patient was adjusted to might not be very comfortable. It might be a position that is even impossible to hold in a completely relaxed state. The examiner may be expecting the patient have some minimum ability to tense sufficient muscles somewhere in order to hold the position. But with many of these poor patients, even that expectation is too much. They are weak, unsteady, and helpless.

What is needed is an improvement which provides solutions to echocardiography examiner's problems with steadying a patient in position during an exam. It is an object of the invention to provide a means to prop and steady the patient for the exam.

SUMMARY OF THE INVENTION

It is an object of the invention to provide a sonography exam bed with one or more pop-up wedges that are disposed to prop a patient on his or her side and in what might be an awkward or hard-to-hold exam position given a patient in poor or weak health.

It is another object of the invention to provide the foregoing sonography exam bed with a heart-region access opening on the left side for exposing reach-up access to the patient's left-side rib-cage heart region, in combination with a ledge on the inboard side to provide anti-sagging support to a thin strip of the patient's rib cage in further combination with at least one pop-up wedge providing concurrently anti-rolling support.

It is an alternate object of the invention to provide a sonography exam bed with one or more access bays formed through the bed's lateral edge and which is(are) filled-in during times of non-use by movable or removable flaps.

It is an additional object of the invention that a sonography exam bed incorporating any inventive combination of the foregoing be provided with one or more folding sections to convert the bed into more like a chair or reclining chair.

It is a further object of the invention that any of the various foregoing options be enhanced with power equipment to drive the movable components (if any) through their movements.

These and other aspects and objects are provided according to the invention in a sonography exam bed having patient support and sonographer access provisions. The inventive bed comprises essentially an elongated bed surface and a prop section. The elongated bed surface extends between left and right sides and a pair of ends. The bed surface is formed with left and right openings such that the bed surface as a whole comprises a relatively enlarged headrest portion, a relatively enlarged bench portion, and a ledge portion longitudinally bridging therebetween and also defining the respective inboard margins of the left and right openings.

The left opening is sized and arranged for exposing from underneath the heart region of a reclining patient's left-side rib cage. The ledge portion is sized sufficiently wide but not unduly narrow for undergirding a thin strip of the patient's rib cage in order to support against sagging into the left opening.

The prop section is attached to the bed for disposition in an up position with respect to the bed surface and located so as to be neither too remote from nor close upon the left opening's inboard margin. That way, the "up" prop section not only to provides a rest for the patient to lean against but also promote proper patient position with respect to the thin strip supported on the ledge portion while otherwise the heart region of the left-side rib cage is substantially exposed from underneath through the left opening. It is an aspect of the invention that the prop section in the up position and the ledge portion cooperatively provide anti-rolling and anti-sagging support for properly reclining patients.

Preferably the right opening is framed in part by a headrest margin and bench margin of the bed surface. These two margins cooperatively define an outboard gap for the right opening. The right opening is useful for standing or sitting access for the sonographer during examination, especially sitting access on the bench margin thereof. So, as long as the prop section is in the up position, the following is an aspect of the invention. That is, the patient exam bed excludes any structure from being arranged restrictive to sonographer access through the outboard gap, or otherwise impede the sonographer's freedom to swing a leg in the right opening or take a seat on the bench margin, in order to obtain not just reasonable airspace clearance through the outboard gap, or above the bed for taking a seat on the bench margin, but also reasonable airspace clearance under the bed through which a sonographer will likely kick or swing a leg or knee.

Optionally, the prop section is attached to the bed for movable adjustment between various positions including various up positions ranging from straight up to shallow or steep angles of inclination. That way, the prop section is adjustable among the various up positions to accommodate different sizes of patients in service of providing patients a rest to lean against while the left-side rib cage spans across the left opening.

The invention might further incorporate a fixing arrangement for releasably fixing the prop section among the various inclined positions. The fixing arrangement is likewise faithful to the exclusion of anything restrictive to sonographer access through the outboard gap, or otherwise impede the sonographer's freedom to swing a leg in the right opening or take a seat on the bench margin, in order to preserve reasonable airspace clearance through the outboard gap, above the bed for taking a seat on the bench margin, and also under the bed where a sonographer will likely kick or swing a leg or knee.

The fixing arrangement can be achieved various ways, including either configured for one-handed operation or hands-free operation. The one-handed version comprises a multiply-notched brace, suspended from the prop section's headrest margin, and a fixed catch pin, secured to the right opening's headrest margin. The hands-free version comprises a coupling system, a drive source mounted under the bed and remote from the prop section, and a foot-operated control unit for operative control over the adjustment of the prop section. This coupling system is arranged to transmit drive input from the drive source to the driven prop section. The coupling system is faithful to the exclusion, with the prop section deployed either straight up or otherwise relatively steeply, of anything restrictive to sonographer access through the outboard gap, or otherwise impedes the sonographer's freedom to swing a leg in the right opening or take a seat on the bench margin, and so preserve reasonable airspace clearance through the outboard gap, above the right opening's bench margin, and also under the bed where a sonographer will likely kick or swing a leg or knee.

The prop section, at least in the straight up position, presents a buffer between the back of a properly reclining patient and the lap of a sonographer seated on the right opening's bench margin. Preferably the prop section is installed for movement furthermore to a fill position in which the prop section presents with the bed surface a generally uninterrupted patient-supporting area along the length of the bed surface adjacent the right side. The bed might further include a filler section for the left opening, that is installed to the backrest section for movement between a fill position, in which the filler section presents with the backrest section a generally uninterrupted patient-supporting area along the length of the backrest section adjacent the left side, and, a deployed position, which opens the left opening.

Additionally, the bed surface might be partitioned into at least a seat section and a movable backrest section that is attached to the bed for movable adjustment between various inclined positions ranging from shallow to steep. The movable backrest section would incorporate the ledge and headrest portions as well as carry with it the prop and filler sections as well as. The seat section would incorporated some of the bench portion.

The prop section is fitted this way for another advantages. That is, with the prop section deployed straight up at least a relatively steeply it presents a vertical edge that is proximate the bench portion of the bed surface. This vertical edge is located relative to the left opening to allow a properly reclining patient's buttocks to project past it (or curl or curve beyond it), free of obstruction from the vertical edge, in order that the prop section may come in contact with the small of the back.

An alternative version of the bed substitutes a second prop section for the filler section. That way, the dual prop sections are deployable such that either one alone or in combination with the other provide anti-rolling support for reclining patients on the ledge of the bed surface. Preferably the prop sections are sized longitudinally compact to achieve sufficient longitudinal stiffness if the fixing arrangements are linked to the corresponding prop section by, alternatively, either a single link, or else asymmetrically disposed links.

A number of additional features and objects will be apparent in connection with the following discussion of preferred embodiments and examples.

BRIEF DESCRIPTION OF THE DRAWINGS

There are shown in the drawings certain exemplary embodiments of the invention as presently preferred. It should be understood that the invention is not limited to the embodiments disclosed as examples, and is capable of variation within the scope of the appended claims. In the drawings, FIG. 1 is a perspective view of a sonography bed having patient support and sonographer access provisions in accordance with the invention, wherein a patient is shown in dashed lines to illustrate a manner of reclining across an access opening in the bed for sonogram examination purposes (eg., echocardiography);

FIG. 2 is a top plan view of the bed in isolation;

FIG. 3 is a reduced scale top plan view comparable to FIG. 2 except showing a more detailed example use of the bed, ie., a view in which both a patient and sonographer are shown in order to illustrate various provisions of the bed in relation to sonogram examinations, patient support, and sonographer access;

FIG. 4 is an enlarged scale perspective view of a sonographer access provision formed in the bed's right side (other portions of bed the being broken away), and additionally showing a lift or "patient support" section therefor, as in a deployed position (in contrast to a closed position);

FIG. 5 is a right side elevational view of the bed;

FIG. 6 is a sectional view taken along line VI—VI in FIG. 2 except showing the drop and lift sections of the bed in closed positions;

FIG. 7 is a partial sectional view, comparable to FIG. 6, except showing the drop and lift sections in deployed positions as in FIGS. 1 through 5;

FIG. 8 is an enlarged scale elevational view taken of detail VIII in FIG. 5;

FIG. 9 is a sectional view taken along line IX—IX in FIG. 8;

FIG. 10 is a perspective view of a sonography bed in accordance with an alternate embodiment of the invention, ie., one which is provided with plural lift sections;

FIG. 11 is a sectional view comparable to FIG. 6 except showing a further embodiment of the invention, ie., one which is provided with power-driven drop and lift sections wherein the closed positions for each are shown in solid lines as, in contrast, the open positions which are shown in dashed lines;

FIG. 12 is right side elevation view of an additional embodiment of the invention, ie., one which has movable sections like a chaise longue or the like, having an inclinable backrest section, an intermediate seat section, and a declinable knee-comfort section.

DETAILED DESCRIPTION OF THE PREFERRED EMBODIMENTS

Figure 13:
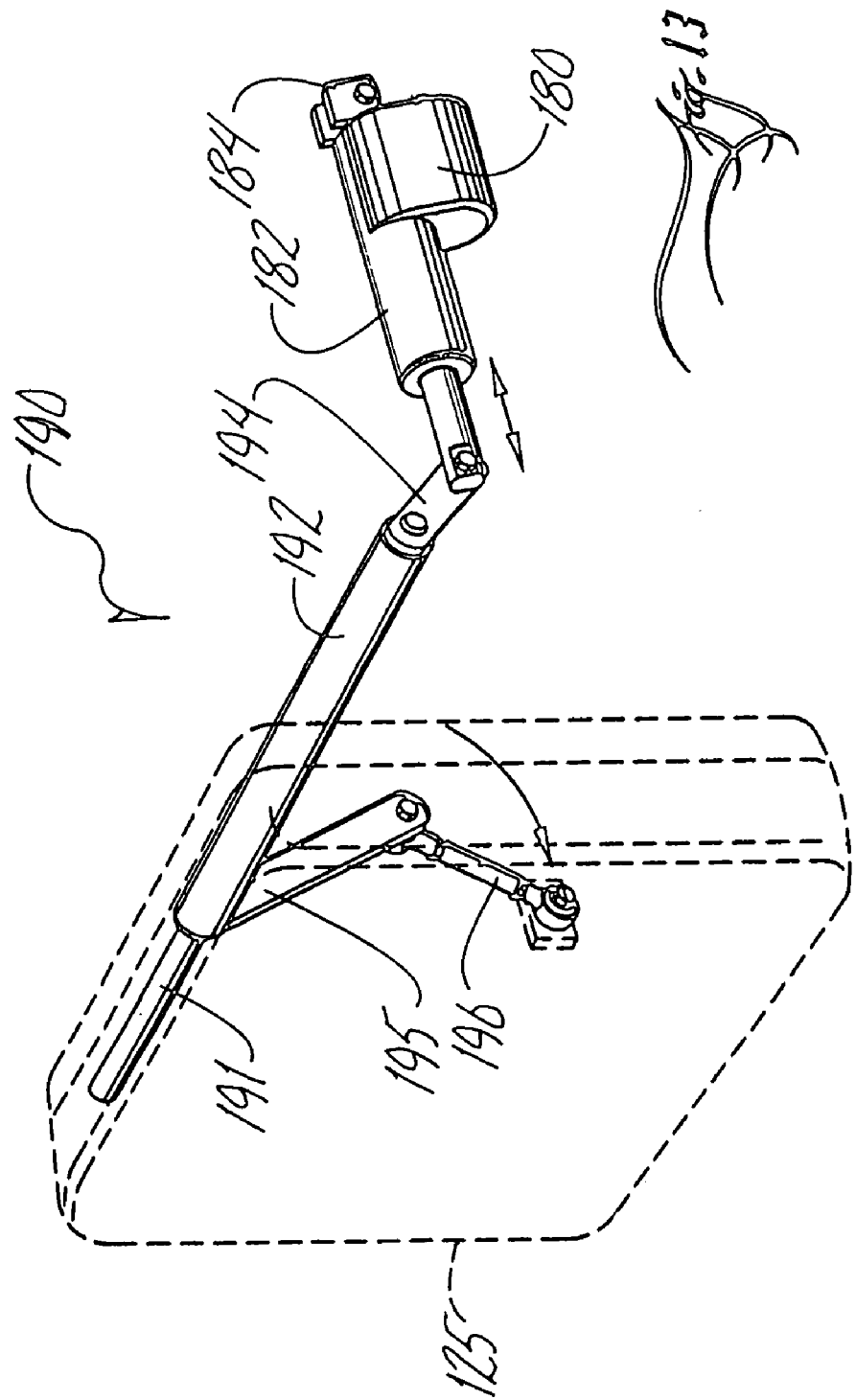
FIG. 13 is an enlarged scale perspective view of an offset linkage system for inter-linking the power-driven drop section with the linear-actuator source of drive power, wherein other portions of the bed are broken away.

FIGS. 1 through 3 show a sonography bed 100 in accordance with the invention comprising a mattress assembly 104 mounted on a wheeled carriage 106.

The mattress assembly 104 comprises a major mattress section 110 being generally rectangular except formed with a pair of lateral openings 80 and 90 spaced from each other by a ledge portion 130. The ledge portion 130 bridges between and/or interconnects a relatively enlarged headrest portion 112 of the major mattress section 110 with a more expansive bench portion 114. The lateral opening 90 in the bed 100's left side is useful as an exam access opening for exposing the heart region of a reclining patient's left-side rib cage. In contrast, the lateral opening 80 on the bed 100's right side is useful for standing or sitting access for the sonographer during examination, especially sitting access.

For each opening 80 and 90, the mattress assembly 104 further includes a movable flap or section 120 and 125. Several of the views (eg., FIGS. 1–5 and 7) show the movable sections 120, 125 in deployed positions, in contrast to FIG. 6 which shows the movable sections 120, 125 in closed positions. In their closed positions, the movable sections 120 and 125 close or "fill" their respective opening 80 or 90 in order to give the bed 100 a full surface, ie., without the openings left "open" by the absence of the shut sections 120 or 125. That way, a full and/or flat mattress assembly 104 (ie., with "filled-in" openings as in FIG. 6)

renders the bed 100 useful for other purposes besides echocardiography alone. Also, a full and/or flat mattress assembly 104 (ie., full and/or flat as in FIG. 6) is easier for getting patients on and off the bed 100.

In their deployed positions the movable sections 120,125 serve various aspects of the invention, but in different ways. The movable section 125 has a deployed position that serves to open the heart-region access opening 90. One way of achieving this is by pivoting movable section 125 on pivot fixtures 127 which allow it to swing down in a dropped position as shown in FIG. 7. Accordingly, movable section 125 is alternatively referred to herein as a "drop" section.

Movable section 120 is likewise pivoted on pivot fixtures 122 except it deploys straight up as well as various angles of inclination. Accordingly, movable section 120 is alternatively referred to herein as a "wedge" section. And so, wedge section 120 serves many purposes. One, it provides anti-roll support by propping or chocking the patient in a selected attitude (of roll). Another, it exposes the leg-access bay 81 (ie., the width of the leg-access opening 80 minus the inboard slice occupied by the deployed wedge section 120). Furthermore, it is a buffer. That is, the wedge section 120 partly shields the sonographer from patients, many of whom have bedsores, fleas or scabies because of prolonged invalidity in unclean environments or the like. Some exam procedures can take as long as twenty minutes.

Given the foregoing, pause can be taken to sketch briefly an echocardiography procedure. At some original time the sonographer receives the patient and makes plans how best to carry out the procedure with that patient. The sonographer might begin with the wedge section 120 in a given angle up while beginning with the drop section 125 in the closed, or level or else "in-fill" position. Now the patient is ready to be exercised to elevate heart rate.

Many patients of this procedure are already sick, frail and weakened, perhaps suffering greatly from the effects of stroke or heart disease. Exercise only exacerbates such patients ability, will and/or anxiety to stretch out across the drop section 125. Some fear it like a trap door. The deployed wedge section 120 not only provides patients a prop to lean against so not to roll out of position but it also provides assurance that the patients are properly shelved on the ledge 130. That is, the ledge 130 undergirds a thin strip of the patient's rib cage in order to support against sagging after the drop section 125 is cut loose to swing down. Again, since many of these patients are weak and fearful, the bed 100 must provide "actual" anti-roll and anti-sagging support as well as should provide, in contrast, an anxiety-alleviating "appearance" of support. Elderly and/or weak patients in particular haven't the strength or endurance with their trunk muscles to keep properly stiff and not sag in the heart-region access opening 90. If a patient starts to shake, the sonographer will probably have to stop the exam and re-start with a new exercise cycle. These patients are usually too physically unfit to be able to do indefinite repeat cycles of exercise, so it is desirable to complete the exam on the first or earliest opportunity available. The wedge section and ledge combination 120 and 130 provide comfort as well as alleviate fear with nervous patients that the exam will be reasonably comfortable.

Once exercise is stopped, the sonographer is practically in a race against the clock to achieve the position shown in FIG. 3. It shows a preferred posture for sonographer and patient during while actual data acquisition is underway. The sonographer has seated himself (or herself) on the bed 100 as shown, to wrap his or her right arm around the patient for ultimately pressing and/or rubbing the probe under the heart region of the patient's left-side rib cage. The sonographer's posture is something like how any of us, while seated, might rub a coffee mug up under a chair in which we're seated. It is an aspect of the invention that the wedge section and ledge combination 120 and 130 cooperatively provide anti-rolling and anti-sagging support.

Given that sketch of an exam procedure, attention can be resumed to describing the invention. FIGS. 6 and 7 show that the wedge and drop sections 120 and 125, while movably attached by means of the pivot fixtures 122 and 127, are preferably attached non-removably, and in contrast to being removable, like withdrawing a drawer or otherwise. This is preferred because it eases the work of finding all the parts again to return the bed 100 back to fully flat. Additionally, this makes the bed 100 more readily adaptable to equipping with power, as more particularly described below in connection with FIGS. 11 through 13.

It is also preferred if the heart-region access opening 90 is sized to measure about thirteen inches (thirty-three cm) square. FIG. 2 shows that the heart-region access opening 90 is framed on three sides by the headrest, ledge and bench portions 112, 114 and 130 of the mattress assembly 104's major mattress section 110. As FIG. 1 or 3 show, the headrest margin 112H props the patient's shoulder, with arm thrust forward, as the bench margin 114H props the patient at the waist or hipbone. Experience finds that a gap between the headrest and bench margins 112H and 114H that measures about thirteen inches (thirty-three cm) is an adequate compromise between short and tall patients. A smaller gap would be preferred for special purpose beds such as pediatric (ie., children's) beds, perhaps something like nine inches (twenty-three cm) or so.

With reference to FIG. 2, line VI—VI extends across the bed 100's width where it includes the openings 80 and 90. Hence the bed 100's overall width can be expressed as the sum of (i) and (ii) the width of the heart-region and leg access openings 90 and 80, plus (iii) the width of the ledge 130. FIG. 6 is the section view taken through line VI—VI except showing the wedge and drop sections 120 and 125 in closed positions. Consequently, the bed 100's overall width can be alternatively expressed as the sum of (i) and (ii) the width of the wedge and drop section 120 and 125 plus (iii) the width of the ledge 130.

FIG. 7 shows the wedge section 120 deployed in its full up position. The pivot fixtures 122 for wedge section 120 pivot the wedge section 120 about a pivot axis that is located out and away from the leg-access opening 80's inboard extreme (as well as below the plane of the major mattress section 110's upper surface 111). Whereas FIG. 6 shows that the width of the wedge section 120 corresponds to the width of the leg-access opening 80, FIG. 7 in contrast shows that the wedge section 120, in its full up position, presents a height less than its full width by the amount it is dropped below the level of the upper surface 111. With that in mind, the overall width of the bed 100 can be expressed by the following equation.

$$\text{Overall Bed Width} = \text{Heart Opening Width} + \text{Height of Wedge} + \text{Drop of Wedge} + \text{Width of Ledge} \quad (1)$$

One design issues concerns the location of the wedge section 120's pivot axis. Since the bed 100 is upholstered, for practical purposes the pivot axis is preferably located somewhere else than at inboard upper extremity of the leg-access opening 80. Neither the upper upholstered mattress surface 111 nor the upper upholstered wedge section surface 121 contains (or has nearby) sufficient solid structure to mount pivot fixtures. Hence, this is done in part to avoid pinch problems between the upholstered cushioning layers of the wedge section and ledge 120 and 130. Conversely, it is preferred to located the wedge section 120's pivot axis reasonably proximate to the inboard upper extremity of the leg-access opening 80 for compactness reasons. Trial and error has ended up with the preferred design to date. For example and without limitation, the pivot axis might be put at two-and-one-half inches (~six cm) outboard from the inboard extreme and about one-half inch (~one-and-one-quarter cm) below the plane of the upper upholstered surface 111 of the major mattress section 110. One consequence of this is that the wedge section 120's upholstered surface 121 glides by the ledge 130. Accordingly, this eliminates pinching between the wedge section 120 and ledge 130. Also, this design allows easier cleaning. In other words, it eliminates a virtual trough which would otherwise only collect and fill with nasty particles shed by patients (usually the invalids who arrive from unclean environments), such as fleas or scabies, or else shaved hair infested with the same. By way of background, hairy-chested patients are shaved on the bed 100 before exercise (usually by a nurse, not the sonographer).

Another design (more accurately, size) issue concerns choosing a "height" for the wedge section 120 to present in its deployed position. To illustrate an example calculation of this using real measurements, consider the following. Assume first that the chosen location for the wedge section 120's pivot axis which is suitably proximate the upper inboard extreme of the leg-access opening 80 nevertheless results in dropping about three inches (eight cm) of the wedge section 120 below the plane of the upper surface 111. So, if it is intended that the wedge section 120's height when deployed is thirteen inches (thirty-three cm), then the width of the wedge section 120 will add up to about sixteen inches (forty-one cm).

The actual choice of "height" for the wedge section 120 (in the deployed position) is an arbitrary choice in part, but there are extremes between too low (in which case the wedge section 120 does not sufficiently support the patient) and too high (in which case it interferes with the reach of the sonographer). To be more particular about being too high, if the wedge section 120 projects up too high then it will interfere with the sonographer's swing of his or her arm when moving swiftly into the exam position in FIG. 3. An unduly high wedge section (eg., 120) might also catch the sonographer in the arm pit while assuming an exam position like FIG. 3, in which case such an "unduly high" wedge section (eg., 120) will cut off blood circulation during the exam, and put the sonographer's arm to sleep.

Hence design of the wedge section 120's deployed height is a balance between being high enough to usefully prop the patient in contrast to not being overdone as to be problematical for the sonographer. Accordingly, trials have found the preferred range to be between about nine and thirteen inches (twenty-three to thirty-three cm) high.

The bed 100's overall width, to digress for a moment, is usually stipulated by market factors, such as depending on what sort of doorways it must navigate through. As a matter of background, exam rooms can be unbelievably cramped. They are almost closets, with narrow doorways to match.

Design of the wedge section 120's width is a balance among the widths of the ledge 130 and heart-region access opening 90 within context of the bed 100's overall width. To better appreciate size issues surrounding the ledge 130's width, consider hypothetically a bed being constructed very narrow (say eighteen inches, or forty-six cm wide) and being limited to being formed with only a heart-region access opening. That is, this hypothetical bed is too narrow to allow inclusion of a leg access opening on the right side. It only has sufficient width to allow inclusion what in the inventive bed 100 corresponds to the ledge 130 and heart-region access opening 90. Assume furthermore that the heart-region access opening in the hypothetical bed is likewise recessed in from the bed's left side by thirteen inches (twenty-three cm). Theoretically this would be a workable bed for right-handed sonographers, but scary for patients. Experience teaches that an echocardiography patient's anxiety ratchets up in proportion to the narrowness of the bed because, such a bed does not appear like it will offer much stability. The patients at that time in their lives are not feeling much like acrobats. A frail elderly women can be imagined as rightfully complaining, 'I'll fall off that bed.' No words could likely assure her that, the bed is as wide as necessary. But to be fair to patient perception, not only does a wider bed reduce patient anxiety, a wider bed truly does offer more stability. Morever, since bed height is adjustable to the individual desires of the sonographer, then the bed ought to be wider for higher height settings. Wider beds offer more certainty to all parties that the patient can be stably stretched out on it.

Now, an easily-perceived shortcoming with this hypothetical bed is that, since there is no right-side or "leg-access" opening, then a right-handed sonographer must sit on the right outboard margin of the bed to do exams. In consequence, his or her legs are pointing his or her waist in the wrong direction. In order to do the exam, the sonographer would have to twist in the trunk, and lean over a lot further. This would cause undue musculoskeletal injury over long enough time. In reality, conventional wisdom has opted for producing the bed wider in combination with providing a leg-access opening in the right side.

However, not everything is simply solved by simply resolving to incorporate a leg-access opening 80 when it comes to sizing the width of the ledge 130. Ideally a designer would prefer to size the heart-region access opening 90 first, then the width of the ledge 130, and finally the height of the deployed wedge section 120, and in summation arrive at the designer's choice for width of bed 100. However, bed width is usually a fixed variable because, there are standardized bed widths that purchasers expect. So, one way at arriving at ledge width is by, starting with a given bed width, choosing a size for the heart-region access opening 90 on the left side of the bed 100 and then a height and drop for the wedge section 120 which summed together will fill a leg-access opening 80 on the right side of the bed. What's left may be reckoned as determining remainder leftover for width of the ledge 130.

In contrast to "ledge width" being a residual factor, there are other considerations. The ledge 130 can't be too narrow because (i) it will not provide meaningful anti-sagging support to even a thin strip of the patient, (ii) it will weaken the construction of the bed 100 especially in double-duty as a "Fowler" panel (eg., what's indicated as 172 in FIG. 12) for a chaise longue configuration, and (iii) there are attendant production problems as well as upholstering problems with too narrow a ledge 130. In contrast, the ledge 130 can't be too wide or else there will be other problems. If the ledge 130 is too wide, then a patient properly positioned with respect to exposing a slice of the left-side rib cage over the heart-region access opening 90, will in fact be too remote from ever leaning against the wedge section 120. In consequence, the wedge section 120's purpose would be nullified. Moreover, the sonographer would have to lean way over further to make up for the waste distance, which would soon provoke musculoskeletal injury or the like from working in an uncomfortable position. An alternative problem is that, if the patient is afforded too wide a ledge 130 to perch on, then he or she might scoot too far away from the heart-region access opening 90 in search of the wedge section 120. The sonographer won't be able to apply the probe to the heart-region of the patient's left-side rib cage because that relevant strip of the rib cage will be perched on the ledge 130, in error. In other words, the heart-region of the rib cage will not be exposed by the heart-region access opening 90 as it should. In view of those considerations, to date a preferred range for width of ledge 130 is between about three and seven inches (~seven and eighteen cm).

The previous mention of "balancing" design choices can now be better appreciated. Choosing a specific size for any factor might change the size of another or several other factors. Each choice has to be tested against whether the size of any other factor is changed beyond an acceptable range. Previously, overall width of the bed was expressed by the equation (1) above. Assume, based on matters previously described, that "width" of the heart-region access opening 90 and the "drop" of the wedge section 120 are fairly settled on at about thirteen inches (thirty-three cm) and three inches (~eight cm) respectively. Accordingly, inserting at least those values in equation (1) results in the following.

$$\begin{array}{cccc} \text{Overall} & & \text{Height} & & \text{Width} \\ \text{Bed} & = 13'' + & \text{of} & + 3'' + & \text{of} \\ \text{Width} & & \text{Wedge} & & \text{Ledge} \end{array}$$

As previously described, it is preferred if the "height" of the wedge section 120 when deployed in the full up position measures in the range of about between nine and thirteen inches (twenty-three to thirty-three cm) because, in that range, it is both useful as a prop while not being so tall as to be an impediment sonographer movement. Consequently, for sake of illustration, if market forces influence the choice of "overall bed width" to be thirty inches (seventy-six cm), and if the "height of wedge [section]" is desired to be thirteen inches (thirty-three cm), then that leaves only one inch (two-and-one-half cm) for the "width of ledge," which is too narrow to be any good. Therefore, if accepted that the "Overall Bed Width" is to remain the same (thirty inches, or thirty-three cm), but if instead the "height of wedge [section]" is changed to be ten inches (twenty-five cm), then that makes "width of ledge" to be four inches (ten cm). These last proportions indeed specify one preferred embodiment of the invention, which may be expressed in full as follows.

$$\begin{array}{cccccc} \text{Overall} & & \text{Heart} & & \text{Height} & & \text{Drop} & & \text{Width} \\ \text{Bed} & & \text{Opening} & & \text{of} & & \text{of} & & \text{of} \\ \text{Width} & = & \text{Width} & + & \text{Wedge} & + & \text{Wedge} & + & \text{Ledge} \\ (30'') & & (13'') & & (10'') & & (3'') & & (4'') \end{array}$$

In contrast, a thirty-six inch (~ninety cm) bed will allow both a thirteen inch "Height of Wedge [section]" (twenty-three cm) and seven inch "Width of Ledge" (eighteen cm). The market seems to prefer, however, a thirty inch (seventy-six cm) bed because it apparently fits the doorways and modest-sized exam rooms better.

Leaving behind size and proportion issues in the lateral dimension, attention can be turned to size and proportion issues in the longitudinal dimension.

FIGS. 2 through 4 (among others) show that the, when the wedge section 120 is up, the leg-access bay 81 is boxed in on three sides by the wedge section 120's bottom panel 123, and the headrest and bench portions 112 and 114 of the major mattress section 110. The spacing between the headrest and bench margins 112L and 112L for the leg-access opening 80 define a longitudinal gap (eg., and which is also about the longitudinal measure of the wedge section 120). This longitudinal measure of the gap is a product of several considerations. First, for purposes of bracing the wedge section 120, only a single brace 160 is preferred, as better shown by FIG. 4. That way, the clearance for movement needed by the single brace 160 can be confined to a single plane. Preferably, this comprises a single lateral plane disposed in common with the headrest margin 112L of the leg-access opening 80. Preferably the bench margin 114L of the leg-access opening 80 is kept clear of structure or mechanisms. These would undesirably impede the sonographer's freedom to swing a leg in the leg-access bay 81 or take a seat upon the bench margin 114L. For the same reasons, the design of the bed 100 as a whole has to eliminate all leg-obstructing structure or equipment from blocking the outboard gap for by the leg-access bay 81. Hence the bed frame structure (eg., indicated as 140 et seq. in FIG. 6) and/or the pivot and bracing mechanisms 122 and 160 for the wedge section 120 all have to be cleared out of that much of the leg-access opening 80 likely to be in path of natural standing or seating movements of the sonographer.

The choice of limiting the bracing system for the wedge section 120 to a single brace 160 influences the choice over how long to make the longitudinal span of the wedge section 120 too. If the wedge section 120 is too long, a single brace 160 on one side is too weak for the job and likewise such an elongated wedge section 120 braced like that is too flimsy. A patient leaning against an excessively elongated wedge section 120 braced only on the headrest side might roll up so hard against the un-braced bench margin 124 that the wedge section 120 would warp. Conversely, for patient-support purposes, a wedge section 120 that is simply very compact in the longitudinal direction will suffice for any given patient. But then of course, there is the need to compensate for different size patients. Thus such compactness in the longitudinal direction has to be wider than necessary for any one patient because, for a population of patients of varying height, they are going to need application of support at varying longitudinal positions relative to the heart-region access opening 90. Accordingly, there are several design factors that must be accounted for and balanced for these purposes.

For patient-support purposes, the sonographer will want the wedge section 120 to apply support against the patient generally opposite the probe. Of course, the probe is going to be applied to the patient on his or her heart region. At minimum, it is preferred that the wedge section 120 apply support at least against the patient's lower back, where it will do more good than if it contacts the patient high up or past the shoulder, where it is less useful. For sonographer seating purposes, the sonographer will want the bench margin 114L to be located where a seating posture in FIG. 3 will allow the sonographer to comfortably extend his or her right arm into the heart-region access opening 90 as shown. Additionally, the longitudinal gap spacing the headrest margin 112L away from the bench margin 114L must be sufficient to allow the sonographer to swing at least his (or her) right thigh in the leg-access bay 81, without being cramped by the headrest margin 112L. Presumably, the sonographer will set the height of the bed 100 something more nearly table height, than chair-seat height, so that less energy is expended while setting down to and standing up from being seated. Furthermore, the sonographer's right leg, while seated, will only be partially flexed, and hence his or her knee will preferably take an elevation below the undergirding structure 140 of the mattress assembly 104 For among other reasons, this allows the leg-access opening 80 to get by with an abbreviated longitudinal gap, and concurrently allows for a more longitudinally-compact wedge section 120 as well.

In striking a balance among all the foregoing size issues, it is preferred if the longitudinal gap of the leg-access opening 80 (and longitudinal extension of the wedge section 120) measures about eleven inches (twenty-eight cm), compared to the thirteen inches (thirty-three cm) for the heart-region access opening 90. More significantly, it is preferred if the bench margin 114L of the leg-access opening 80 extends along a line about two inches (five cm) forward of the bench margin 114H for the heart-region access opening 90. The wedge section 120 will correspondingly have a bench-side terminus 124 that likewise two inches (five cm) or so short of the bench margin 114H of the heart-region access openings. FIG. 3 shows that this geometry allows a properly outstretched patient's buttocks to curl around, free of interference from the wedge section 120's bench-ward terminus 124. The relative proportions of these things achieves all the following advantages:—namely, it is more comfortable to the patient, it assists the sonographer with finding proper positioning for the patient, and the wedge section is better configured to apply support where wanted (in the lower back) than where not (against the buttocks).

To shift focus at this point away from issues of relative proportions, the description that follows next focuses instead on structural and construction issues. In FIG. 6, the mattress assembly 104 is undergirded by—for example and without limitation—an undergirding framework of rectangular tubing 140. The undergirding 140 carries an upholstered cushioning layer 142 that has upholstered foam or cushion material laying atop a substrate 144 of plywood or other suitable material including without limitation particle board, wood-product composite, or other synthetic planar materials. The wheeled carriage 106 comprises another rectangular-tube frame assembly that forms an II-shaped cart or bogie 146, including caster-style wheels, upon which is anchored a sole centrally-disposed telescoping leg 148. The cart 146's (or bogie's) configuration in the II-shape provides relative elimination of obstacles to trip or impede the movements of the sonographer around the bed 100 as well as in-and-out of the various access openings 80 and 90. The telescoping leg 148 allows adjustment of the mattress 104's elevation. The leg 148 might be mechanically driven by an electric actuator or the like or user-actuated by treadle pump or the like (not shown).

FIGS. 8 and 9 show a non-limiting example of a latching system 150 for the drop section 125. It has latch pins 152 that retract from latching positions (eg., oppositely extending or projecting positions) from corresponding sockets 141 (see FIG. 7) formed in the mattress assembly 104's rectangular-tube undergirding 140 that extend along the headrest and bench margins 112H and 114H of the heart-region access opening 90. The drop section 125 can be unlatched swiftly, easily as twisting a lever handle 154, so that the drop section 125 is thus freed to swing down from its latched (ie., closed or in-fill) position to its deployed position, in which it hangs suspended by pivot pins 127. The drop section 125 has a rectangular-tube undergirding forming an open square. The outboard-most tube provides mounting for the hand-lever 154 as shown. The lever 154 changes at a right angle into a shaft 156. The shaft 156 drives a crank arm 157, which is welded thereto or otherwise secured. The crank arm 157 extends from the shaft 156 to a terminal end which secures the origin-ends of a pair of pull cables 158. The pull cables 158 loop around idlers to terminate in attachments to the back ends of the opposite latch pins 152. Accordingly, twisting the lever's handle 154 (eg., clockwise in FIG. 9) causes the pull cables 158 to pull or retract the latch pins 152 out and free of the sockets 141.

To turn now to the wedge section 120 and its brace 160, FIG. 4 shows better that the brace 160 is produced as a slender bar having a lower edge formed with a series of notches 162. As the case with the heart-region access opening 90, the leg-access opening 80 is rimmed by portions of rectangular-tube undergirding 140 that undergirds the major mattress section 110 as whole. The headrest and bench margins 112L and 112H thereof carry attached stops 162 at the outboard extremes of the leg-access opening 80 for limiting the downward swing of the wedge section 120 into a level or "in-fill" position. In use, the brace 160 allows a sonographer freedom to adjust the wedge section 120 to one of several available use angles. To do this, the sonographer simply lifts up the wedge section 120 and rests any one of the brace 160's notches 160 in a catch pin 166 of a ring link. To readjust the wedge section 120, the sonographer simply thrusts the brace 120 to move the "caught" notch 162 off the catch pin 166, then readjusts the wedge section 120 to a succeeding desired angle and thus height, and finishes by pushing the brace 160 back down so that an appropriate one of the notches 162 catches onto the catch pin 166 of the ring link. Thus the wedge section 120 is adjustable between an in-fill or closed position (FIG. 6) and various degrees of deployed positions (as, for example, the 90° straight up position shown by FIG. 7). In use, the sonographer might pre-set the angle before the exam. Once the patient is stretched out across the bed 100 and/or during the exam, the sonographer might make quick adjustments to the angle to get it more exactly where the sonographer wants it.

The inventive wedge section and ledge combination 120 and 130 provide advantages over the prior art. A weak and unsteady patient can contribute greater to the effort to hold an uncomfortable position with the use of the wedge section 120 than without. Hence the sonography bed 100 in accordance with the invention includes inventive structure functioning in inventive ways to provide advantages only provided as applicants have brought to use.

FIG. 10 is a perspective view of a sonography bed $100^1$ in accordance with an alternate embodiment of the invention. It has dual movable wedge sections $120^0$ and $120^0$ spaced by a ledge or strip portion $130^1$ of the major mattress section $110^1$ extending between and connecting a first portion $112^1$ and second portion $114^1$ of the major mattress section $110^0$. Whereas the drawing shows a mirror-opposite construction of the dual wedge sections $120^0$ and $120^1$, alternatively the dual wedge sections $120^0$ and $120^0$ could be offset, or else sized differently and so on. The dual wedge sections $120^0$ and $120^1$ form an access bay or slip-in space for the sonographer(s) from both or either of the left and right sides. The dual wedge sections $120^0$ and $120^0$ (in the deployed positions as shown) serve to stabilize a patient in proper position in right or left decubitus position (not shown) during certain vascular or abdominal sonograms. This bed configuration $100^1$ more particularly is advantageous for various gynecological, vascular (eg., leg/crotch arteries) and renal (eg., kidney) exams. In such exams, the patients lie on their sides and examiners have a use for such a double-wedge section configuration, especially if the double-wedge sections $120^0$ and $120^1$ are not centered but relatively nearer one end of the bed $100^1$ than the other.

FIG. 12 and its companion views FIGS. 11 and 13 comprise series that depict another embodiment of the sonography bed $100^2$ in accordance with the invention. This version of the bed $100^2$ has power-driven movable sections that move as shown in FIG. 11 or 12.

More particularly, this FIG. 12 version of the bed $100^2$ has movable wedge and drop sections 120 and 125 as does the FIG. 1 bed. In contrast, the FIG. 12 bed $100^2$ furthermore has a movable backrest section 170 (sometimes referred to as a "Fowler" panel), an intermediate seat section 172, and optionally a movable knee-comfort section 174. It is optional if the seat section 172 is fixed level for all times. In the drawings, the seat section 172 is illustrated movable at least into an extreme up-lifted position as shown in dashed lines in FIG. 12.

FIG. 12's movable backrest section 170 is formed with the wedge and drop sections 120 and 125 (as better shown by FIG. 11). The folding backrest section 170 allows conversion of the bed $100^2$ into more like a chair or reclining chair. The folding backrest section 170 is movable between a level position, as FIG. 12 shows in solid lines, through various angles of inclination, an example being shown in dashed lines.

Both FIGS. 11 and 12 show that the various movable sections are linked power drives, or more preferably, linear actuators. FIG. 13 shows better that a representative linear actuator 180 has a drive rod 182 which can be driven in extension and retraction strokes as desired. In FIG. 13, this actuator 180 is shown interlinked with the drop section 125 for illustration of how the other movable sections might be inter-linked with their corresponding drive actuator.

In FIG. 13, the actuator 180 extends between the terminal end of the drive rod 182 and an opposite stop end 184. The stop end 184 includes a bracket for securing to a given anchorage. In this view, the anchorage comprises the rectangular-tube undergirding 140 on the opposite side of the bed $100^2$ from the heart-region access opening 90. The drive rod 182 is inter-linked with the movable drop section 125 by a linkage system 190 that is mounted on an axle 191. The linkage system 190 includes a cylindrical sleeve 192 mounted for revolution about the axle 191, an input arm 194 and output arm 195 fixed to the opposite ends of the sleeve 192, and a connecting link 196 to the drop section 125. The axle 191 is fixed beneath the undergirding 140 of the mattress assembly 104 such that the sleeve turns on the same axis as the drop section 125's pivot axis 127 (see FIG. 11). The input arm 194 is fixed to one end of the sleeve 192 and extends to a pinned connection with the actuator 180's drive rod 182. The output arm 195 is fixed to the opposite end of the sleeve 192 and extends to a pinned connection with one end of the connecting link 196, the opposite end thereof being in a pinned connection with a bracket on the underside of the drop section 125 as shown.

In order that the sonographer not be impeded with standing in the leg-access bay 81 and/or siting on the bench margin 114L thereof, all the linear actuators and associated linkage systems have to be arranged and attached to the bed 1002 so as to not interfere with the sonographer's freedom to stand or sit so. In other words, all structure and mechanisms have to be designed to give clearance to that much of the leg-access bay 81 likely to be in path of natural standing and seating movements of the sonographer, including not just the outboard gap defined by the leg-access bay 81 or else the perch on the bench margin 114L for the sonographer's seat, but also any airspace under the bed $100^2$ which a sonographer will likely kick or swing a leg. This clearance is achieved in part by inclusion of the sleeve 192. It allows a designer to offset two parallel planes, neither illustrated, but one containing the input arm 194 and the other containing the output arm 195. That way, the mounting of the linear actuator 180 can be chosen by design to be as remote and spaced away as desired from the respective movable section it drives (eg., 125 in FIG. 13).

FIG. 13 shows the linear actuator 180 in an extreme retracted position, such that the drop section 125 is moved to its deployed or down position. The linear actuator 180 is controllable to drive its drive rod 182 into an extreme extended position so that the drop section 125 is driven into its shut or "in-fill" position, as shown in FIG. 11 in solid line. To date it is preferred without limitation to utilize electric-powered linear actuators 180. This affords the convenience of producing a controller out of electric switches or other such electric-circuit devices.

Incorporating power equipment provides the sonographer with several advantages. One is mechanical advantage, ie., the linear actuators 180 do the heavy work. Two is remote control. The drop section 125 in particular can be operated without the sonographer having to be within reach of a lever (eg., as shown by FIG. 8 or 9). For instance, the sonographer might prefer to leave the drop section 125 shut or flat after assisting the patient onto the bed $100^2$ until after the sonographer has come around to the opposite side. That way, the sonographer might simply leave the drop section 125 shut until the sonographer has such time to take a seat in the leg-access bay 81 on the opposite side. Additional advantages of power-driven movable sections include virtually infinite choices of angle adjustment, and this is especially desirable for the wedge section 120, in contrast to the set number of choices defined by the teeth in the notched brace 160 in FIG. 4.

It is preferred to provide the FIG. 12 bed $100^2$ with dual control units (not shown), each having full control over any and all of the linear actuators as the other. The distinction between the control units is that, preferably one is handheld and hand-operated while the other is mounted and foot-operated. The handheld unit can be carried about or be rested in places where the sonographer chooses, so it is there where he or she puts it when he or she wants it. In distinction, the foot-operated control unit is mounted somewhere low (as on the II-shaped cart or bogie 146) but preferably accessible by a seated sonographer in the leg-access opening 80. That way, as soon as the sonographer swings into the leg-access opening 80 and/or takes a seat on the bench margin 114L thereof, all control over the movable sections are thereafter at his or her disposal on the foot-operated unit. Among other things, the foot-operated unit frees both hands of the sonographer from management over any movable section's position. Hands-free controls in combination with fast-acting actuators may also speed up the time in which the sonographer can get things done around the bed $100^2$. In a stress echo test, the window of opportunity after exercise is stopped is about forty-five seconds. Time is paramount. The time saved by a hands-free controlled, power-driven drop section is advantageously significant.

The invention having been disclosed in connection with the foregoing variations and examples, additional variations will now be apparent to persons skilled in the art. The invention is not intended to be limited to the variations specifically mentioned, and accordingly reference should be made to the appended claims rather than the foregoing discussion of preferred examples, to assess the scope of the invention in which exclusive rights are claimed.

We claim:

1. A patient exam bed comprising:
   an elongated bed surface extending between left and right sides and a pair of ends, and being formed with left and right openings such that the bed surface comprises a relatively enlarged headrest portion, a relatively enlarged bench portion, and a ledge portion longitudinally bridging therebetween and also defining the respective inboard margins of the left and right openings, wherein said left opening provides underneath exposure of the heart region of a reclining patient's left-side rib cage, and wherein said ledge portion provides undergirding support for a thin strip of the patient's rib cage in order to support against sagging into the left opening;
   a drop flap for temporarily filling the left opening in order to present with said bed surface a generally uninterrupted patient-supporting area along the length of the bed surface adjacent the left side, and pivoted along a given margin of the left opening for dropping out of said left opening by swinging down in order to open said left opening;
   a latching mechanism for temporarily latching the drop flap in position of temporarily filling the left opening, said latching mechanism including a manual actuator which is actuated by a one-handed or hands-free actuation so a sonographer has at least a hand and arm not occupied with dropping the drop flap and free for steadying the patient during actuation, and which actuator when actuated unlatches the drop flap for automatically dropping out of the left opening in order that the sonographer not be any further occupied with dropping the drop flap other than actuating the actuator; and
   a prop section for the right opening attached to the bed for disposition in an up position with patient's ribs' the bed surface and provide a rest for the patient to lean against with respect to the thin strip supported on the ledge portion;
   whereby said prop section in the up position and said ledge portion cooperatively provide anti-rolling and anti-sagging support for reclining patients.

2. The patient exam bed of claim 1 wherein, with said prop section in the up position, said patient exam bed excludes structure restrictive to the sonographer's freedom to swing a leg in the right opening or thereafter take a seat on the bench portion.

3. The patient exam bed of claim 2 wherein said prop section is attached to the bed for movable adjustment ranging from straight up to shallower angles of inclination with respect to the ledge portion.

4. The patient exam bed of claim 3 further comprising:
   a fixing arrangement for releasably fixing the prop section temporarily immovable.

5. The patient exam bed of claim 4 wherein:
   the fixing arrangement is either configured for one-handed operation and comprises a multiply-notched brace, suspended from the prop section's headrest margin, and a fixed catch pin, secured to a margin of the right opening defined by the headrest portion, or alternatively is configured for hands-free operation and comprises a coupling system, a drive source mounted under the bed and remote from the prop section, and a foot-operated control unit for operative control over the adjustment of the prop section.

6. The patient exam bed of claim 3 wherein said prop section, at least in the straight up position, presents a buffer between the back of a reclining patient and the lap of the sonographer when seated on the bench portion with a leg swung in the right opening.

7. The patient exam bed of claim 3 wherein the prop section is installed for movement furthermore to a fill position in which the prop section presents with said bed surface a generally uninterrupted patient-supporting area along the length of the bed surface adjacent the right side.

8. The patient exam bed of claim 1 wherein:
   the actuator comprises either a depressible lever or push button, either of which affords actuation by a bump from a single hand, forearm, elbow or hip.

9. The patient exam bed of claim 8 wherein the given margin of the left opening to which the drop flap is pivoted comprises the inboard margin.

10. A patient exam bed comprising:
    an elongated bed surface extending between left and right sides and a pair of ends, and being formed with left and right openings such that the bed surface comprises a relatively enlarged headrest portion, a relatively enlarged bench portion, and a ledge portion bridging longitudinally therebetween as well as laterally spacing the left and right openings, wherein said left opening provides exposure from underneath to the heart region of a reclining patient's left-side rib cage, and wherein said ledge portion provides undergirding support for a thin strip of the patient's rib cage in order to support against sagging into the left opening;
    a filler section for the left opening and installed to the bed for movement between a fill position in which the filler section presents with said bed surface a generally uninterrupted patient-supporting area along the length of the bed surface adjacent the left side, and, a retracted position which opens said left opening and provides a sonographer an unobstructed reach to the reclining patient's left-side rib cage;
    a powered drive system for moving the filler section comprising a drive source, a coupling system coupling the filler section to the bed and having an input connection connected to the drive source for driving the coupling system to cycle the filler section between the fill and retracted positions, and a manual control-signal entry device which is operated by a one-handed or hands-free operation so the sonographer has at least a hand and arm not occupied with entering control signals to the drive system and thus free for steadying the patient during the retraction of the filler section; and,
    a prop section for the right opening attached to the bed for movable adjustment ranging from straight up to shallower angles of inclination with respect to the ledge portion and being located to provide a rest for the patient to lean against with patient's ribs' the thin strip supported on the ledge portion, and the heart region of the patient's left-side rib cage substantially exposed from underneath through the left opening when the filler section is retracted;
    whereby said prop section and ledge portion cooperatively provide anti-rolling and anti-sagging support for reclining patients.

11. The patient exam bed of claim 10 wherein, with the prop section deployed up, said patient exam bed excludes structure restrictive to the sonographer's freedom to swing a leg in the right opening or thereafter take a seat on the bench portion.

12. The patient exam bed of claim 10 further comprising:
a fixing arrangement for releasably fixing the prop section temporarily immovable.

13. The patient exam bed of claim 12 wherein:
the fixing arrangement is either configured for one-handed operation and comprises a multiply-notched brace, suspended from the prop section's headrest margin, and a fixed catch pin, secured to a margin of the right opening defined by the headrest portion, or alternatively is configured for hands-free operation and comprises a coupling system, a drive source mounted under the bed and remote from the prop section, and a foot-operated control unit for operative control over the adjustment of the prop section.

14. The patient exam bed of claim 10 wherein said prop section, if deployed either straight up or otherwise relatively steeply, presents a buffer between the back of a reclining patient and the lap of the sonographer when seated on the bench portion with a leg swung in the right opening.

15. The patient exam bed of claim 10 wherein said filler section is pivoted along a given margin of the left opening for dropping out of said left opening by swinging down in order to open said left opening.

16. The patient exam bed of claim 15 wherein the given margin of the left opening to which the filler section is pivoted comprises the inboard margin.

17. A patient exam bed comprising:
an elongated bed surface extending between left and right sides and a pair of ends, and being formed with left and right openings such that the bed surface comprises a relatively enlarged first portion, a relatively more expansive relatively enlarged second portion and a ledge portion bridging longitudinally therebetween, as well as laterally spacing the left and right openings, for undergirding a reclining patient's torso;
a fill section for temporarily filling the left opening, directly attached to the bed for movement between a fill position flush with the bed surface and a retracted position which opens the left opening in order to provide underneath exposure of the heart region of a reclining patient's left-side rib cage while at the same time the ledge portion provides undergirding support for a thin strip of the patient's rib cage in order to support against sagging into the left opening;
a prop section for the right opening, directly attached to the bed for movement between a fill position flush with the bed surface and various deployed up positions;
wherein said patient exam bed excludes structure that is restrictive to a sonographer's freedom to swing a leg in the right opening or thereafter take a seat on the second portion when the prop section is deployed steeply up;
wherein said prop section is deployable to provide anti-rolling support for reclining patients.

18. The patient exam bed of claim 17 further comprising:
a powered drive system for the fill section comprising a drive source, a coupling system coupling the fill section to the bed and having an input connection connected to the drive source for driving the coupling system to cycle the fill section between the fill and retracted positions, and a manual control-signal entry device which is operated by a one-handed or hands-free operation so the sonographer has at least a hand and arm not occupied with entering control signals to the drive system and thus free for steadying the patient during retraction of the fill section.

19. The patient exam bed of claim 18 wherein:
the fill section is pivoted along a given margin of the left opening for dropping out of said left opening to the retracted position by swinging down in order to open said left opening; and
said patient exam bed further comprises a latching mechanism for temporarily latching the fill section in the fill position, said latching mechanism including a manual actuator which is actuated by a one-handed or hands-free actuation so the sonographer has at least a hand and arm not occupied with dropping the drop flap and thus free for steadying the patient during actuation, and which actuator when actuated unlatches the drop flap for automatically dropping out of the left opening in order that the sonographer not be any further occupied with dropping the drop flap other than actuating the actuator.

* * * * *